United States Patent [19]

Boden et al.

[11] Patent Number: 5,283,237
[45] Date of Patent: Feb. 1, 1994

[54] USE IN PERFUMERY OF 2(1-VINYL-5-HEXENYL) CYCLOPENTANONE, A PROCESS FOR PREPARING SAME, AND PROCESS INTERMEDIATES

[75] Inventors: Richard M. Boden, Ocean; William J. Fylak, Loch Arbour; Joseph A. McGhie, South Orange; Charles E. J. Beck, Summit, all of N.J.

[73] Assignee: International Flavors & Fragrances Inc., New York, N.Y.

[21] Appl. No.: 84,603

[22] Filed: Jul. 1, 1993

[51] Int. Cl.$^5$ .............................................. A61K 7/46
[52] U.S. Cl. ...................................................... 512/8
[58] Field of Search ............................ 512/8; 508/379

[56] References Cited

FOREIGN PATENT DOCUMENTS 3216085 11/1983 Fed. Rep. of Germany .......... 512/8
57-188540 11/1982 Japan .................................. 512/8

OTHER PUBLICATIONS

Bortolin and Musco, "Co-Oligomerization of Butadiene And Cyclic Ketones Catalyzed By Palladium Phosphine Compleses", Journal of Molecular Catalysis, vol. 22, (1984), pp. 319-326 (abstracted at Chemical Abstracts vol. 100, 1984, No. 174303z.
1991-1992 Catalog, Bedoukian Research Inc. 21 Finance Drive, Danbury, Conn. 06810-4192, p. 2, Item 410, "Apritone", CAS No. 68133-79-9.

Primary Examiner—James H. Reamer
Attorney, Agent, or Firm—Arthur L. Liberman

[57] ABSTRACT

Described is the 2(1-vinyl-5-hexenyl)cyclopentanone having the structure:

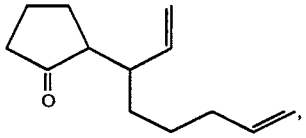

a process for preparing same by reacting the compound having the structure:

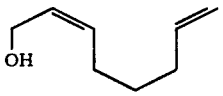

with the compound having the structure:

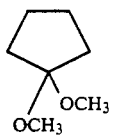

and then heating the resulting intermediate, and organoleptic uses of the compound having the structure:

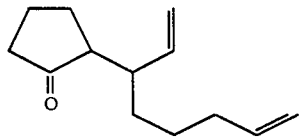

in perfumery.

6 Claims, 3 Drawing Sheets

GLC PROFILE FOR EXAMPLE II.

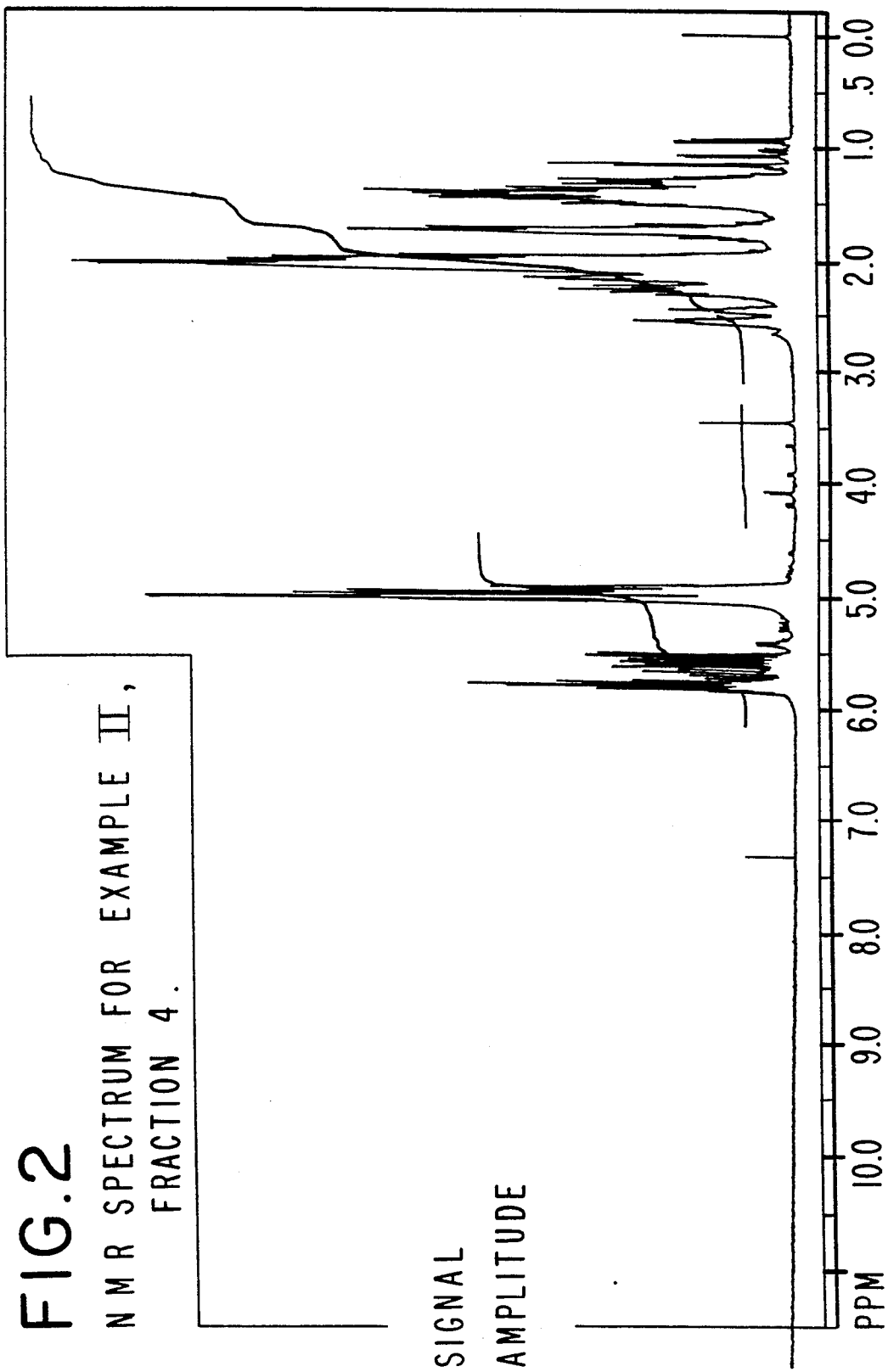
FIG.2 NMR SPECTRUM FOR EXAMPLE II, FRACTION 4.

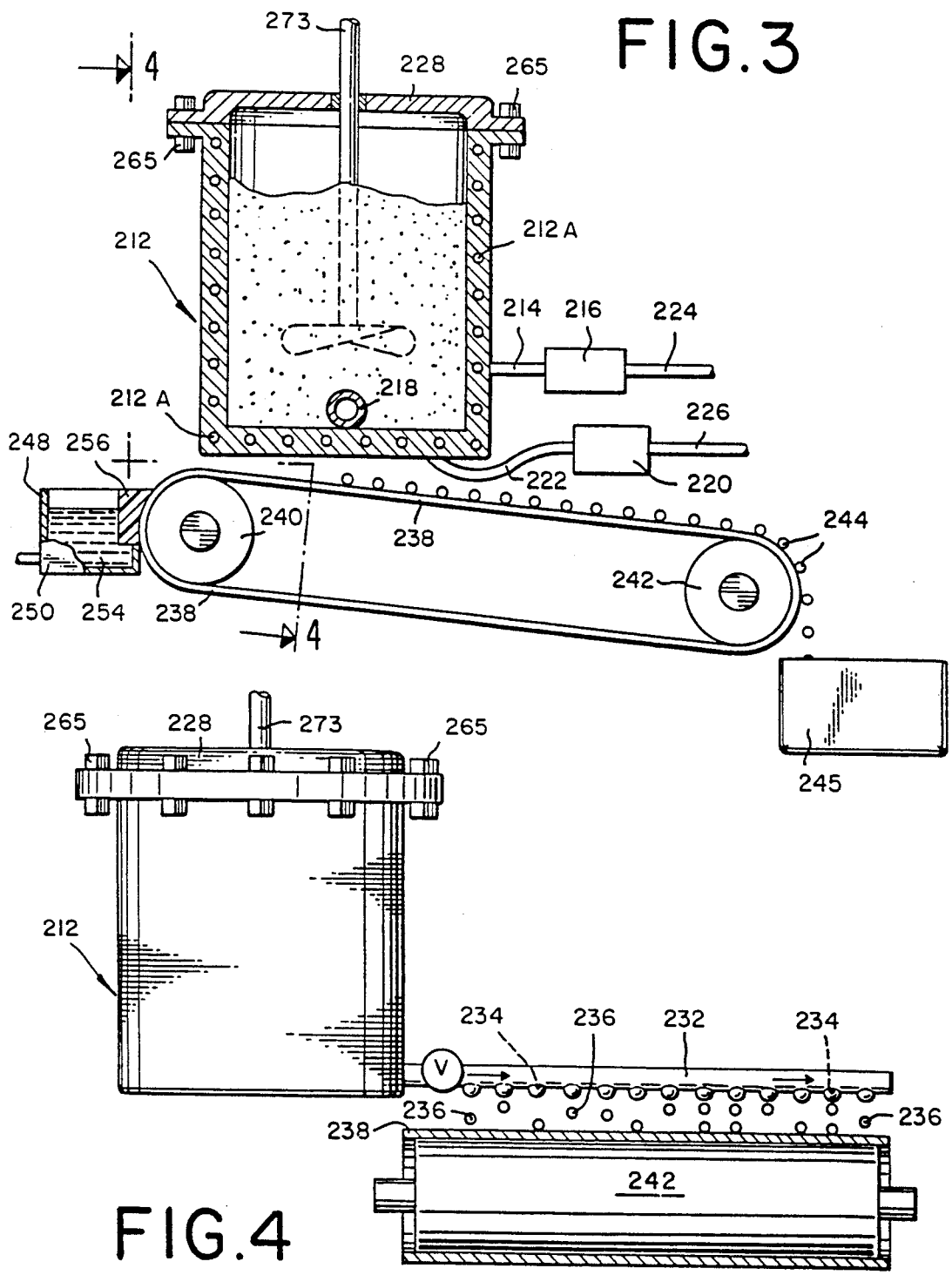

USE IN PERFUMERY OF 2(1-VINYL-5-HEXENYL) CYCLOPENTANONE, A PROCESS FOR PREPARING SAME, AND PROCESS INTERMEDIATES

BACKGROUND OF THE INVENTION

This invention relates to the 2(1-vinyl-55-hexenyl) cyclopentanone having the structure:

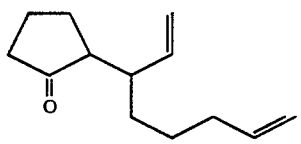

and the process for preparing same by reacting the ketal having the structure:

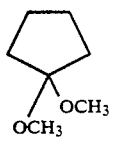

with the unsaturated alcohol having the structure:

and then heating the resulting intermediate and uses thereof in augmenting or enhancing the aroma of perfume compositions, perfumed articles and colognes. This invention also relates to the novel intermediates having the structures:

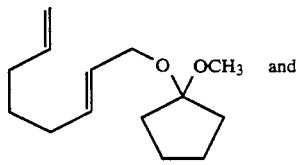

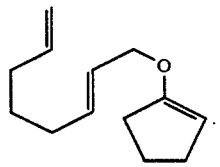

Inexpensive minty, peppery, pineapple and jasmine aromas with natural oily and waxy undertones are highly desirable in the art of perfumery. Many of the natural materials (e.g., natural jasmine oil) which provide such fragrances and contribute such desired nuances are high in cost, vary in quality from one batch to another and/or are generally subject to the usual variations of natural products. Indeed, at times, jasmine oil itself has been impossible to obtain at any reasonable price.

In the course of the last five years, particularly, an increasing amount of attention has been devoted to the preparation and utilization of artificial perfumes and odor modifying agents possessing the aroma attributes of jasmine oil.

Cyclopentanone derivatives having jasmine undertones are known in the perfumery trade. Thus, "APRITONE®" manufactured by Bedoukian Research Inc. of 21 Finane Drive, Danbury, Conn. 06810-4192 has the structure:

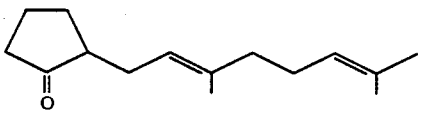

and is described as having a "peach-apricot aroma with jasmine undertones".

Bortolin and Musco, Journal of Molecular Catalysis, Volume 22 (1984) pages 319–326 shows a syntheses which yields a very small amount of the compound having the structure:

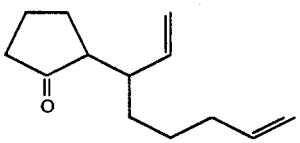

according to the reaction:

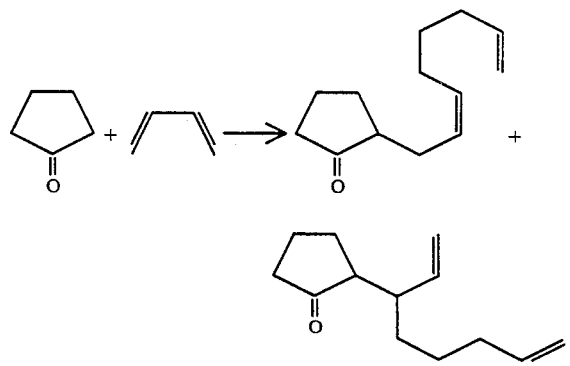

whereby the major material produced in this reaction has the structure:

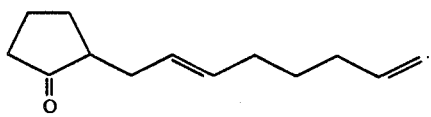

Nothing in the prior art, however, discloses an efficient process for producing the compound having the structure:

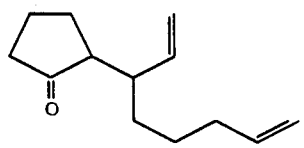

or discloses the use in perfumery particularly as a jasmine substitute of the compound having the structure:

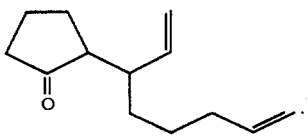

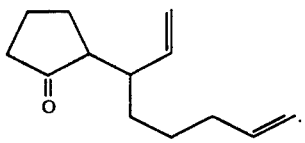

Figure 1:
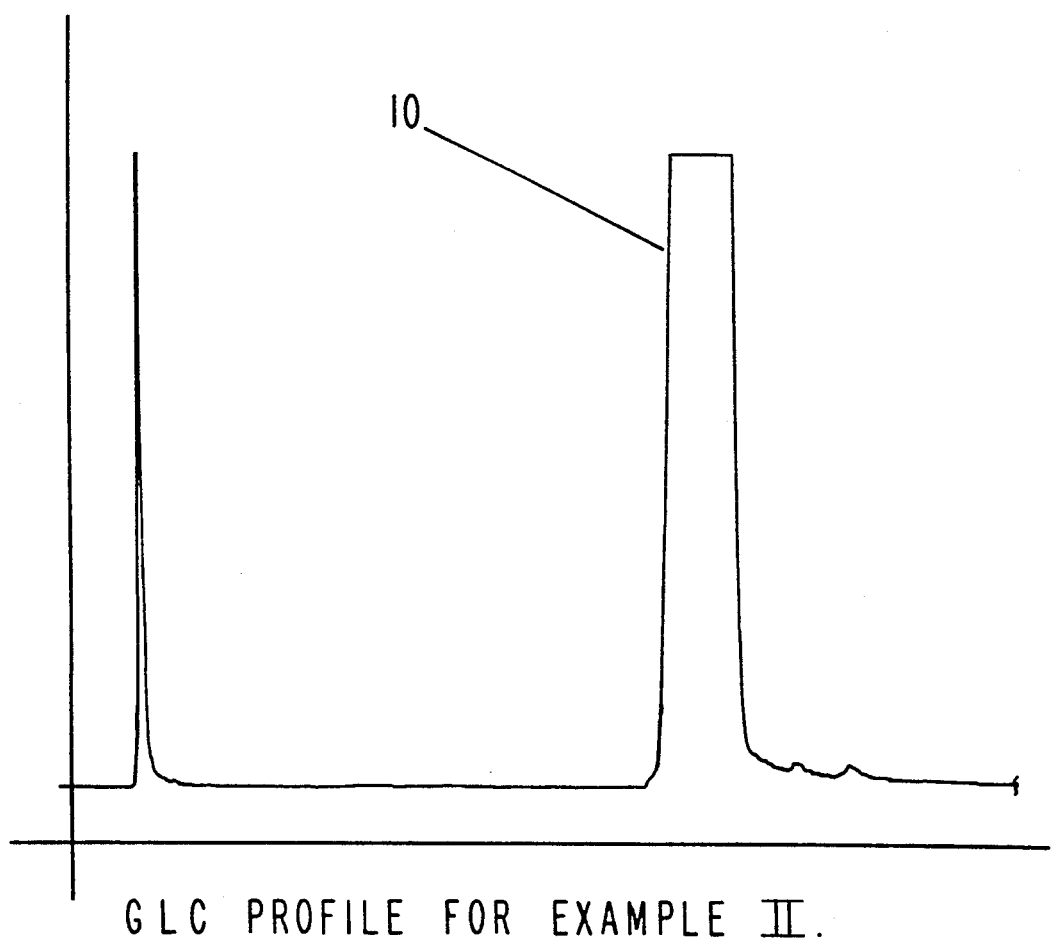
FIG. 1 is the GLC profile for the reaction product of Example II containing the compound having the structure.

FIG. 2 is the NMR spectrum for distillation Fraction 4 of the reaction product of Example II for the compound having the structure:

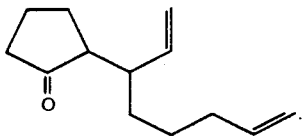

FIG. 3 represents a cut-away side elevation view of apparatus used in forming perfumed polymers which contain imbedded therein the 2(1-vinyl-5-hexenyl)cyclopentanone of our invention.

FIG. 4 is a front view of the apparatus of FIG. 3 looking in the direction of the arrows.

DETAILED DESCRIPTION OF THE DRAWINGS

FIG. 1 is the GLC profile for the reaction product of Example II (Conditions: SE-30 column programmed from 100°-220° C. at 8° C. per minute). The peak indicated by reference numeral 10 is the peak for the compound having the structure:

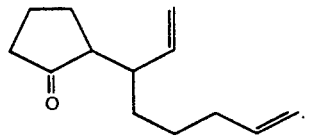

Referring to FIGS. 3 and 4, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and, in addition, polyethylene) such as pellets useful in the formation of plastic articles, useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 3 and 4, in particular, the apparatus used in producing such elements comprises a device for forming a polymer containing perfume, e.g., polyethylene or polyethylene/polyvinyl acetate or mixtures of same or polypropylene, which comprises a vat or container 212 into which the polymer taken alone or in admixture with other copolymers and the perfuming substance which is the compound having the structure:

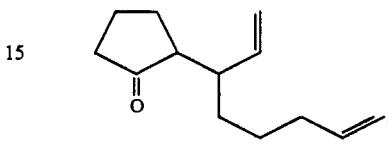

the 2(1-vinyl-5-hexenyl)cyclopentanone of our invention and other compatible perfume materials. The container is closed by means of an air-tight lid 228 and clamped to the container by bolts 265. A stirrer 273 traverses the lid or cover 228 in an air-tight manner and is rotatable in a suitable manner. A surrounding cylinder 212A having heated coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 saybolt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains the 2(1-vinyl-5-hexenyl)cyclopentanone of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes, and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass sto flow outwardly through conduit 232 having a multiplicity of orifices 234 adjacent to the lower side thereof. The outer end of the conduit 232 is closed so that the liquid polymer in intimate admixture with at least the 2(1-vinyl-5-hexenyl)cyclopentanone of our invention will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the 2(1-vinyl-5-hexenyl)cyclopentanone of our invention, through the orifices 234 at a rate which will insure the formation of droplets 236 which will fall off downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention relates to provision of the compound having the structure:

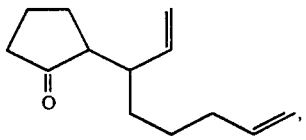

the 2(1-vinyl-5-hexenyl)cyclopentanone of our invention and uses thereof in augmenting or enhancing the aroma of perfume compositions, colognes and perfumed articles (e.g., solid or liquid anionic, cationic, nonionic or zwitterionic detergents, fabric softener compositions, fabric softener articles, perfumed articles and cosmetic powders).

Also described is a process for preparing the 2(1-vinyl-5-hexenyl)cyclopentanone having the structure:

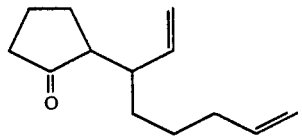

using as starting materials the compound having the structure:

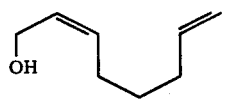

and a compound having the structure:

wherein $R_1$ and $R_2$ are the same or different lower alkyl, for example, methyl (e.g., with the starting material having the structure:

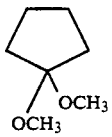

Thus, the compound having the structure:

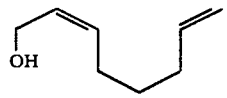

is first reacted with a compound defined according to the structure:

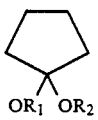

according to the reaction:

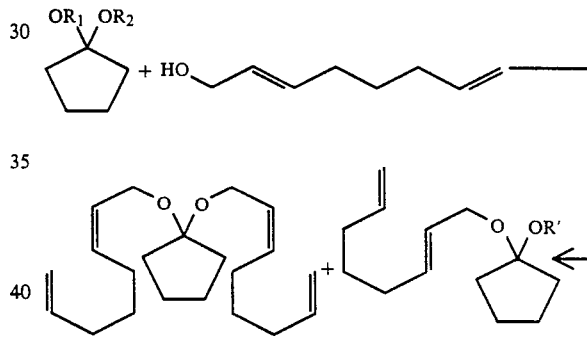

The resulting intermediate defined according to the structure:

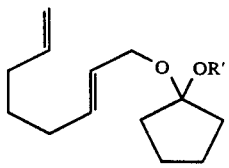

wherein $R'$ is $R_1$ or $R_2$ or the compound having the structure:

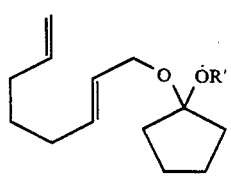

represents a mixture of compound having the structures:

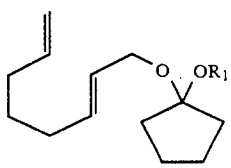

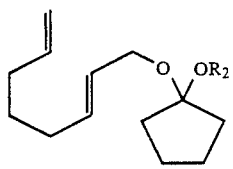

is then decomposed according to the reaction:

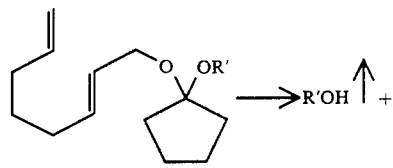

in order to form the enol ether having the structure:

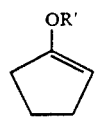

as well as the enol ether having the structure:

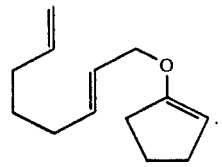

The enol ether formation is carried out at a temperature of between about 80° C. up to about 95° C. The resulting enol ether having the structure:

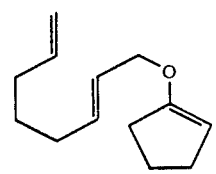

is then rearranged at 165°–180° C. in basic media using, for example, a sodium alkoxide such as sodium methoxide to form the 2(1-vinyl-5-hexenyl)cyclopentanone having the structure:

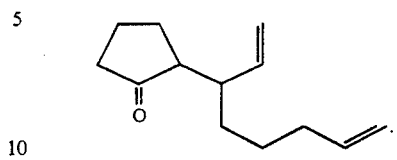

The rearrangement mechanism may be shown, thusly, and is a Claisen-type rearrangement:

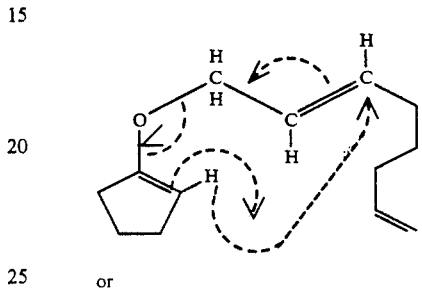

or

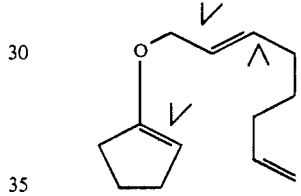

More specifically, the genus of compounds defined according to the structure:

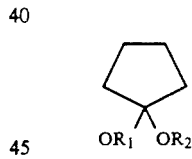

may first be prepared by reacting cyclopentanone with an alcohol having the structure:

R'OH wherein R' is lower alkyl or the compound having the structure:

R'OH represents a mixture of alcohols having the structures:

R₁OH and

R₂OH wherein $R_1$ and $R_2$ are different lower alkyl according to the reaction:

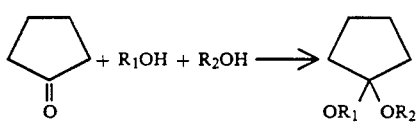

In the alternative, cyclopentanone can be reacted with trimethylorthoformate and methanol in admixture in the presence of acetyl chloride according to the reaction:

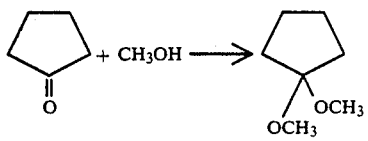

at a temperature in the range of from about 35° C. up to about 50° C. in order to yield the compound having the structure:

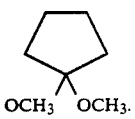

For example, the compound having the structure:

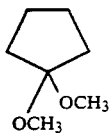

may then be fractionally distilled and used as a reactant in the subsequent reaction with the compound having the structure:

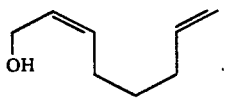

In carrying out the reaction:

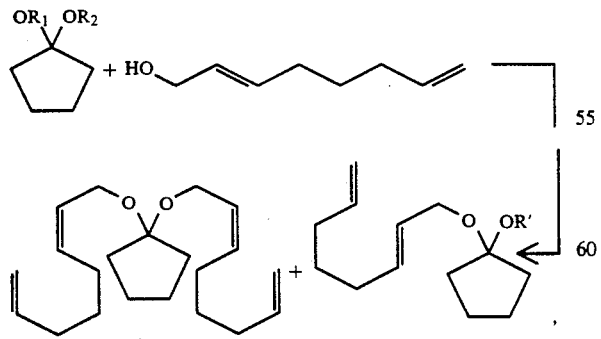

this reaction takes place preferably in the presence of critic acid with the weight ratio of citric acid present in the reaction mass being about 0.01:1. The reaction is carried out at a temperature in the range of about 80° C. up to about 90° C. The resulting intermediate having the structure:

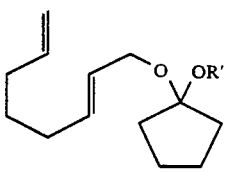

is then decomposed in the same apparatus as was used to form it according to the reaction:

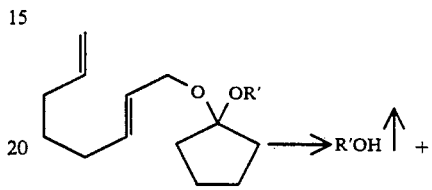

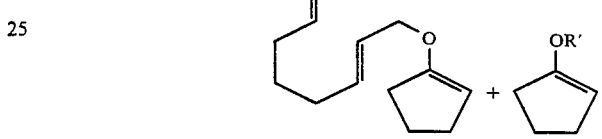

while distilling using, for example, a Bidwell apparatus to distill out alcohol reaction product, that is, alcohol having the structure: R'OH.

After all of the alcohol distillate having the structure:

R'OH is collected, and all the enol ether having the structure:

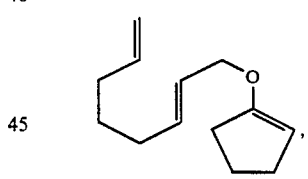

the enol ether is then rearranged according to the reaction:

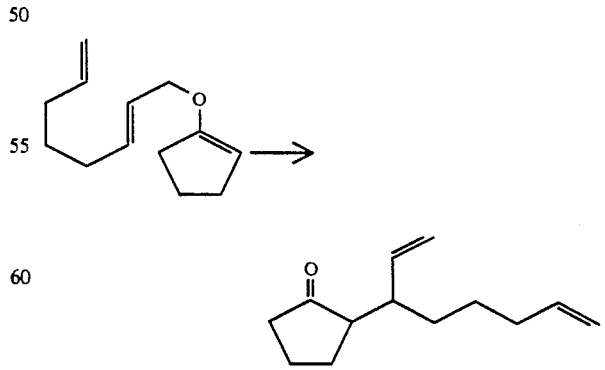

in the presence of base such as a sodium alkoxide or sodium methoxide at a temperature in the range of from about 165° C. up to about 180° C. As stated, supra, the rearrangement mechanism is shown, thusly:

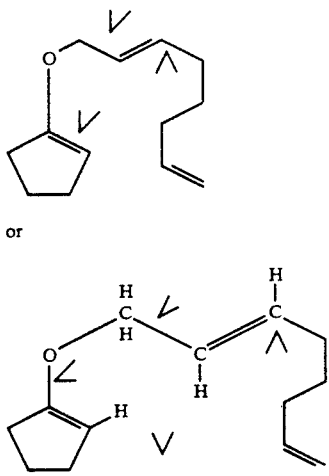

or

The resulting reaction product is worked up in the usual manner such as by washing with water and fractional distillation, for example, fractional distillation at a vapor temperature of 95° C. and a pressure of 2.0 mm/Hg.

The resulting 2(1-vinyl-5-hexenyl)cyclopentanone having the structure:

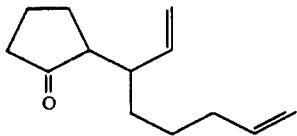

has a minty, peppery, pineapple and jasmine aroma with natural oily and waxy undertones.

The 2(1-vinyl-5-hexenyl)cyclopentanone of our invention and one or more auxiliary perfume ingredients including, for example, alcohols, aldehydes, terpenic hydrocarbons, ketones (other than the 2(1-vinyl-5-hexenyl)cyclopentanone of our invention), esters, nitriles, lactones, natural essential oils, synthetic essential oils, mercaptans and alkyl mercapto derivatives may be admixed so that the combined odors of the individual components produce a pleasant and desired fragrance, particularly in the jasmine type fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual compositions which contribute to their particular olfactory, characteristics, however, the over-all sensory effect of the perfume composition will be at least the sum total of the effects of each of the ingredients. Thus, the 2(1-vinyl-5-hexenyl)-cyclopentanone of our invention can be used to alter, modify or enhance the aroma characteristics of a perfume composition, for example, by utilizing or moderating the olfactory reaction contributed by another ingredient in the composition.

The amount of the 2(1-vinyl-5-hexenyl)cyclopentanone of our invention which will be effective in perfume compositions as well as in perfumed articles (e.g., solid or liquid detergents, soaps, fabric softener compositions, drier-added fabric softener articles, optical brightener compositions, perfumed polymers, textile sizing agents and colognes) depends on many factors, including the other ingredients, their amounts and the effects which are desired. It has been found that perfume compositions containing as little as 0.1% of the 2(1-vinyl-5-hexenyl) cyclopentanone of our invention or even less (e.g. 0.005%) can be used to impart a minty, peppery, pineapple and jasmine aroma with natural oily and waxy undertones to soaps, cosmetics, anionic, cationic, nonionic or zwitterionic detergents, fabric softener compositions, fabric softener articles, optical brightener compositions, textile sizing compositions, perfumed polymers or other products. The amounts employed can range up to 70% of the fragrance components and will depend on considerations of cost, nature of the end product, the effect desired on the finished product and the particular fragrance sought.

The 2(1-vinyl-5-hexenyl)cyclopentanone of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture produced from said perfumed polymers. When used as an olfactory component of a perfumed article as little as 0.2% of the 2(1-vinyl-5-hexenyl)cyclopentanone of our invention will suffice to impart an intense minty, peppery, pineapple and jasmine aroma with natural oily and waxy undertones to jasmine perfume formulations. Generally, no more 6% of the 2(1-vinyl-5-hexenyl)cyclopentanone of our invention based on the ultimate end product is required in the perfumed article composition. Accordingly, the range of the 2(1-vinyl-5-hexenyl) cyclopentanone of our invention in the perfumed article is from about 0.2% by weight of the 2(1-vinyl-5-hexenyl) cyclopentanone of our invention based on the perfumed article up to about 6% by weight based on the perfumed article. In addition, the perfume composition or fragrance composition of our invention can contain a vehicle or carrier for the 2(1-vinyl-5-hexenyl)cyclopentanone of our invention. The vehicle can be a liquid, such as a non-toxic alcohol, e.g., ethyl alcohol, a non-toxic glycol, e.g., propylene glycol or the like. The carrier can also be an absorbent solid, such a gum (e.g., gum arabic, guar gum or xanthan gum) or components for encapsulating the composition (such as gelatin) as by coacervation; or components for forming a polymer wall around a liquid perfumed center such as a urea/formaldehyde prepolymer.

Our invention also relates to the utilization of controlled release technology for the controlled release of perfumes into gaseous environments from polymers such as mixtures of epsilon polycaprolactone polymers and polyethylene which poly epsilon caprolactone polymers are defined according to at least one of the structures:

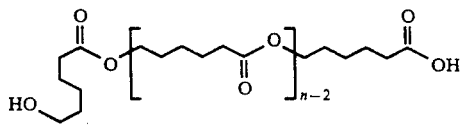

-continued and/or

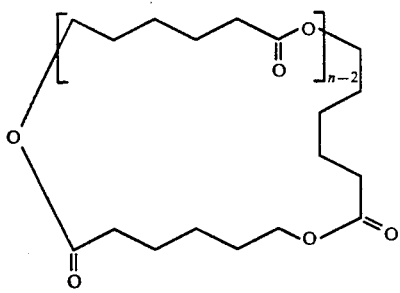

wherein "n" is from about 50 up to about 1,200 with the proviso that the average "n" in the system varies from about 150 up to about 700 according to the mathematical statement:

$$[700 \geq \bar{n} \geq 150]$$

with the term n being the average numer of repeating monomeric units for the epsilonpolycaprolactone polymer. The perfumed material's release rate from such polymer mixture is close to "zero order". As a general rule, the release rate in a polymeric matrix is proportional to $t^{\frac{1}{2}}$ until about 60% of the functional fluid is released from the polymeric matrix. The release rate thereafter is related exponentially to time as a general rule according to the equation:

$$dM_1/dt = k_1 e^{-k_2 t}$$

wherein $k_1$ and $k_2$ are constants. According to Kydonieus, "Controlled Release Technologies: Methods, Theory, and Applications" (cited, supra), the amount of perfume composition released is proportional to time as long as the concentration of perfume material present, e.g., the 2(1-vinyl-5-hexenyl)-cyclopentanone of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release rate being constant (zero order) as long as the surface area does not change during the erosion process. This is the case with the polymers containing the 2(1-vinyl-5-hexenyl)cyclopentanone of our invention.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMO-PLASTIC POLYMERS PL-300 AND PCL-700". These polyepsilon caprolactone polymers are composed of a repeating sequence of non-polar methylene groups and relatively polar ester groups. The average number of repeating monomeric units varies between 150 and 700 depending on the particular "PLC" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such hydroquinone or compounds having the formula:

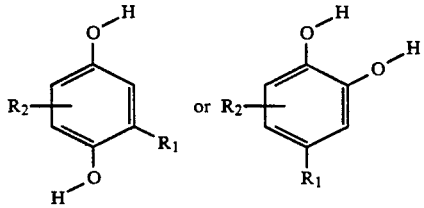

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do no interfere with the functional fluids dissolved and/or adsorbed into the polymeric matrix.

The method for incorporating the 2(1-vinyl-5-hexenyl)-cyclopentanone of our invention or perfume compositions containing same into the polymers may be according to the technique of U.S. Pat. No. 3,505,432 issued on Apr. 7, 1970 (specification for which is incorporated by reference herein) or U.S. Pat. No. 4,247,498 issued on Jan. 27, 1981, the disclosure of which is incorporated by reference herein.

Thus, for example, a first amount of liquid polyethylene/-polyepsilon caprolactone polymer mixture (50:50) is mixed with the 2(1-vinyl-5-hexenyl)cyclopentanone of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700:polyethylene in molten form is admixed with; a high percentage of the 2(1-vinyl-5-hexenyl)cyclopentanone of our invention and the mixture is solidified in the form of pellets or beads. These pellets or beads thus contain a high percentage of the 2(1-vinyl-5-hexenyl)cyclopentanone of our invention and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, polymers specified and described in United Kingdom Patent Specification No. 1,589,201 published on May 7, 1981.

In accordance with the present invention the 2(1-vinyl-5-hexenyl) cyclopentanone of our invention is added to the polymer in a large closed container or drum which is maintained under controlled temperature conditions while the polymer is in a melted condition. The polymer is mixed with the 2(1-vinyl-5-hexenyl) cyclopentanone of our invention under agitation as illustrated in FIGS. 3 and 4 described in detail, supra.

The following Example II serves to illustrate a process for preparing the 2(1-vinyl-5-hexenyl)cyclopentanone of our invention.

The examples following Example II are illustrative of the organoleptic utilites of the 2(1-vinyl-5-hexenyl)cyclopentanone of our invention.

All parts and percentages given herein are by weight unless otherwise specified.

EXAMPLE I

PREPARATION OF DIMETHYL KETAL OF CYCLOPENTANONE

Reaction

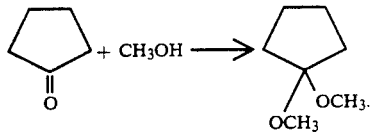

Into a 5 liter flask equipped with stirrer, condenser, thermometer, Bidwell solvent collection trap and heating mantle are charged the following materials:

1000 grams methanol;
1800 (18.85 moles) of trimethylorthoformate; and
1500 grams (17.85 moles) cyclopentanone.

The resulting mixture is heated to 40° C. collecting methylformate. Over a period of 20 minutes, 25 grams of acetyl chloride is added to the reaction mass. At the end of the acetyl chloride addition, 20 cc of distillate are collected. The reaction is then maintained with stirring for a period of 14 hours at 40° C. The total amount of distillate collected is 205 cc. 33 Grams of 25% alcoholic sodium methoxide is then added to the reaction mass. The reaction mass is then distilled yielding the produce having the structure:

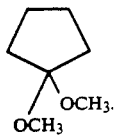

EXAMPLE II

PREPARATION OF 2(1-VINYL-5-HEXENYL)CYCLOPENTANONE

Reaction

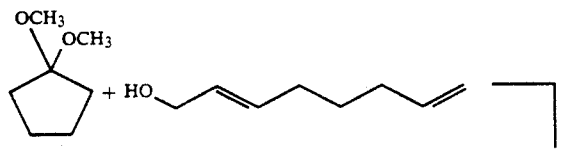

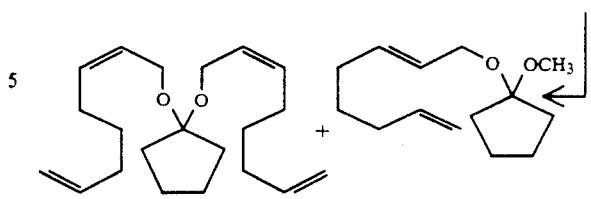

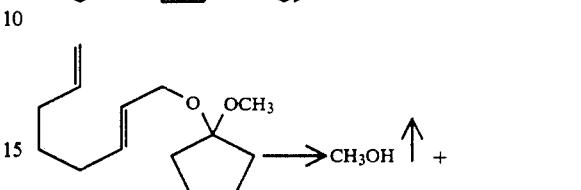

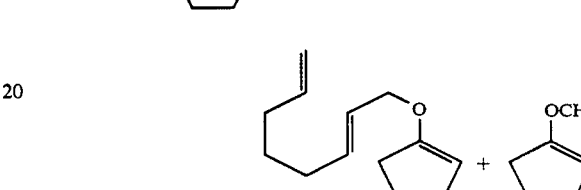

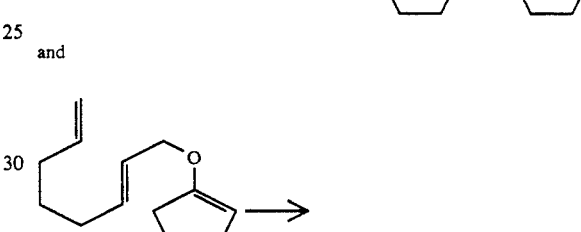

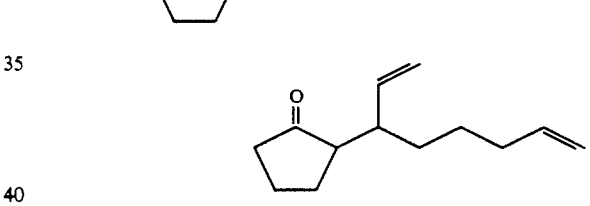

Into a 3 liter reaction vessel are placed 910 grams cyclopentanone ketal having the structure:

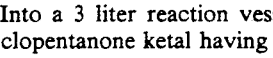

prepared according to Example I; 882 grams (7 moles) of the compound having the structure:

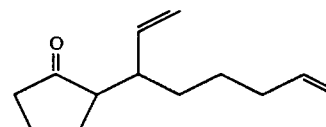

and 21 grams (0.05 moles) of acetic acid. The reaction mass is heated to 80°-90° C. and maintained with stirring at 80°-90° C. for a period of two hours. At the end of the two hour period, 20 grams of citric acid is added to the reaction mass with stirring. The reaction mass is then maintained at 90° C. for a period of 2.5 hours period, the Bidwell apparatus is hooked up and methyl alcohol is collected via the Bidwell trap. Methyl alcohol is continued to be collected while maintaining the reaction mass at 90°-95° C. for a period of three hours. During this three hour period 50 cc of methyl alcohol are collected.

The reaction mass is cooled to 50° C. and 76 grams (0.05 moles) of 25% sodium methoxide in methanol is added to the reaction mass. The reaction mass is then heated to 175° C. and maintained at 175° C. for a period of seven hours.

At the end of the seven hour period, the reaction mass is cooled to room temperature, and washed with 1000 cc volume of water and then distilled on a "rushover" column yielding the following fractions:

| Fraction No. | Vapor Temp. (°C.) | Liquid Temp. (°C.) | Vacuum mm/Hg. Pressure |
|---|---|---|---|
| 1 | 78/85 | 90/96 | 4.5/5.0 |
| 2 | 100 | 120 | 3.0 |
| 3 | 105 | 120 | 3.0 |
| 4 | 105 | 159 | 3.0. |

FIG. 1 is the GLC profile of Fraction 4 of this distillation containing the compound having the structure:

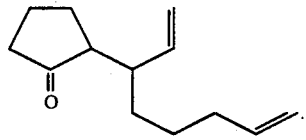

Fraction 4 is redistilled on a Goodloe column yielding the following fractions:

| Fraction No. | Vapor Temp. (°C.) | Liquid Temp. (°C.) | Vacuum mm/Hg. Pressure |
|---|---|---|---|
| 1 | 75/85 | 96/105 | 2.3/2.5 |
| 2 | 95 | 108 | 2.0 |
| 3 | 95 | 100 | 2.0. |

Fractions 2 and 3 are bulked and bulked distillation Fractions 2 and 3 have a minty, peppery, pineapple and jasmine aroma with natural oily and waxy undertones.

NMR analysis (FIG. 2) is indicative of the fact that bulked Fractions 2 and 3 are the compound having the structure:

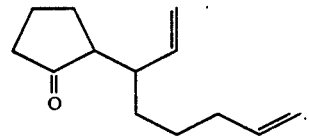

EXAMPLE III

GALBANUM/JASMINE FORMULATION

The following galbanum/jasmine formulation is prepared:

| Ingredients | Parts by Weight |
|---|---|
| 3,3-Dimethyl-1-penten-4-oyl cyclohexane | 24.0 |
| 2(1-Vinyl-5-hexenyl)cyclopentanone prepared in accordance with Example II, supra. | 32.0 |
| Rose oxide | 3.0 |
| Amyl cinnamic aldehyde | 4.0 |
| Geraniol | 12.0 |
| Citronellol | 5.0 |
| Ylang oil | 12.0 |
| Phenylethyl acetate | 14.2 |
| Beta-phenylethyl alcohol | 12.0. |

The resulting product is an excellent "galbanum/jasmine" formulation. The 2(1-vinyl-5-hexenyl)cyclopentanone of Example II imparts to this formulation minty, peppery, pineapple and jasmine topnotes with natural oily and waxy undertones. Accordingly, the perfume formulation of this example can be described as "a galbanum and jasmine aroma with minty, peppery, pineapple and jasmine topnotes and natural oily and waxy undertones".

EXAMPLE IV

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| The compound having the structure: 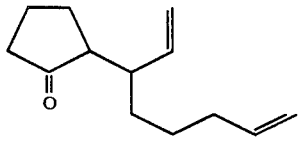 (bulked distillation Fractions 2 and 3) prepared in accordance with Example II, supra. | A minty, peppery, pineapple, and jasmine aroma with natural oily and waxy undertones. |
| Perfume composition of Example III. | A galbanum and jasmine aroma with minty, peppery, pineapple and jasmine topnotes and natural oily and waxy undertones. |

EXAMPLE V

PERFUMED LIQUID DETERGENTS

Concentrated liquid detergents (lysine salt of n-dodecylbenzene sulfonic acid as more specifically described in U.S. Patent No. 3,948,818 issued on Apr. 6, 1976 incorporated by reference herein) with aroma nuances as set forth in Table I of Example IV, supra, are prepared containing 0.10%, 0.15%, 0.20%, 0.25%, 0.30% and 0.35% of the substance set forth in Table I of Example IV, supra. They are prepared by adding and homogeneously mixing the appropriate quantity of substance set forth in Table I of Example IV, supra, in the liquid detergent. The detergents all possess excellent aromas as set forth in Table I of Example IV, supra, the intensity increasing with greater concentrations of substance as set forth in Table I of Example IV, supra.

EXAMPLE VI

PREPARATION OF COLOGNES AND HANDKERCHIEF PERFUMES

Compositions as set forth in Table I of Example IV, supra, are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 90% and 95% aqueous food grade ethanol solutions). Distinctive and definitive fragrances as set forth in Table I of Example IV, supra, are imparted to the colognes and to the handkerchief perfumes at all levels indicated.

EXAMPLLE VII

PREPARATION OF SOAP COMPOSITIONS

One hundred grams of soap chips (per sample) IVORY ® produced by the Procter & Gamble Company of Cincinnati, Ohio), are each mixed with one gram samples of substances set forth in Table I of Example IV, supra, until homogeneous compositions are obtained. In each of these cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV, supra.

EXAMPLE VIII

PREPARATION OF SOLID DETERGENT COMPOSITIONS

Detergents are prepared using the following ingredients according to Example I of Canadian Patent No. 1,007,948 (incorporated herein by reference):

| Ingredient | Percent by Weight |
|---|---|
| NEODOL ® 45-11 (a $C_{14}$-$C_{15}$ alcohol ethoxylated with | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table I of Example IV, supra. Each of the detergent samples has excellent aromas as indicated in Table I of Example IV, supra.

EXAMPLE IX

Utilizing the procedure of Example I at column 15 of U.S. Patent No. 3,632,396 (the disclosure of which is incorporated herein by reference), nonwoven cloth substrates useful as drier-added fabric softening articles of manufacture are prepared wherein the substrate, the substrate coating, the outer coating and perfuming material are as follows:
1. A water "dissolved" paper ("Dissolvo Paper");
2. Adogen 448 (m.p. about 140° F.) as the substrate coating; and
3. An outer coating having the following formulation (m.p. about 150° F.):
   57% - $C_{20}$-$C_{22}$HAPS
   22% - isopropyl alcohol
   20% - antistatic agent
   1% - of one of the substances as set forth in Table I of Example IV, supra.

Fabric softening compositions prepared according to Example I at column 15 of U.S. Patent No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV, supra, is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example IV, supra.

EXAMPLE X

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of polymer is dissolved in the alcohol. The following ingredients are added to the PVP/VA alcoholic solution:

| Ingredients | Weight Percent |
|---|---|
| Dioctyl substrate | 0.03 |
| Benzyl alcohol | 0.10 |
| Dow Corning 473 fluid (prepared by the Dow Corning Corporation) | 0.10 |
| TWEEN ® 20 surfactant (prepared by ICI America Corporation | 0.03 |
| One of the perfumery sustances as set forth in Table I of Example IV, supra | 0.10 |

The perfume substances as set forth in Table I of Example IV, supra, add aroma characteristics as set forth in Table I of Example IV, supra, which are rather intense and aesthetically pleasing to the users of the soft-feel, good-hold hair sprays.

EXAMPLE XI

CONDITIONING SHAMPOOS

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT ® 755N polymer (manufactured by GAF Corporation of 140 West 51st Street, New York, N.Y. (5.0 weight percent) is admixed with 0.1 weight percent sodium sulfite and (1.4 weight percent) polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table I of Example IV, supra, is added to the mixture. The resulting mixture is cooled to 40° C. and blending is carried out for an additional one hour in each case. At the end of this blending period, the resulting material has a pleasant fragrance as indicated in Table I of Example IV, supra.

EXAMPLE XII

Each of the fragrance materials of Table I of Example IV, supra, are added to a 50:50 weight:weight mixture of low density polyethylene: polyepsilon caprolactone PCL-700 forming pellets with scents as set forth in Table I of Example IV, supra.

75 Pounds of a 50:50 mixture of PCL-700 polyepsilon caprolactone (manufactured by the Union Carbide Corporation of New York, N.Y. having a melting point of about 180°-190° F.: low density polyethylene, are heated to about 250° F. in a container of the kind illustrated in FIGS. 2 and 3. 25 Pounds of each of the fragrance materials as set forth in Table I of Example IV, supra, is then quickly added to the liquified polymer mixture, the lid 228 is put in place and the agitating means 273 are actuated. The temperature is then raised to about 250° F. and the mixing is continued for 5-15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table I of Example IV, supra, are thus formed. Analysis demonstrates that the pellets contain about 25% of the perfume material so that almost no losses in the scenting substance did occur. These pellets may be called "master pellets"

50 pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table I of Example IV, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table I of Example IV, supra.

What is claimed is:

1. A perfume composition comprising a perfume base and intimately admixed therewith an aroma augmenting, enhancing or imparting quantity of the 2(1-vinyl-5-hexenyl)cyclopentanone having the structure:

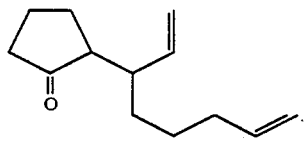

2. A cologne base comprising water, ethanol and an aroma imparting quantity of the 2(1-vinyl-5-hexenyl)cyclopentanone having the structure:

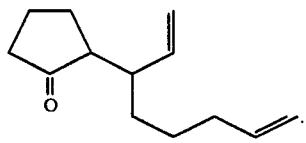

3. A perfumed article comprising a perfumed article base and intimately admixed therewith an aroma augmenting, enhancing or imparting quantity of the 2(1-vinyl-5-hexenyl)cyclopentanone having the structure:

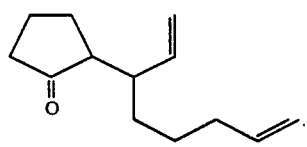

4. A perfumed polymer comprising a microporous polymer containing in the interstices thereof an aroma imparting quantity of the 2(1-vinyl-5-hexenyl)cyclopentanone having the structure:

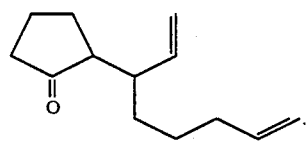

5. A process for augmenting, or enhancing or imparting an aroma in or to a perfume composition, a cologne or a perfumed article comprising the step of intimately admixing with said perfume composition, cologne or perfumed article an aroma augmenting, enhancing or imparting quantity of the 2(1-vinyl-5-hexenyl)cyclopentanone having the structure:

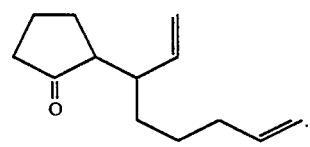

6. The process of claim 5 wherein the perfumed article is a solid or liquid anionic, cationic, nonionic or zwitterionic detergent.

* * * * *